T867015

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED OCTOBER 28, 1969

867 O.G. 1093

762,241
MEANS AND METHOD OF HEMODIALYSIS
Charles H. Benton, 755 Ridge Road,
Rochester, N.Y. 14650
Filed Sept. 16, 1968. Published Oct. 28, 1969
Int. Cl. A61m *5/00*
U.S. Cl. 128—214
1 Sheet Drawing. 9 Pages Specification

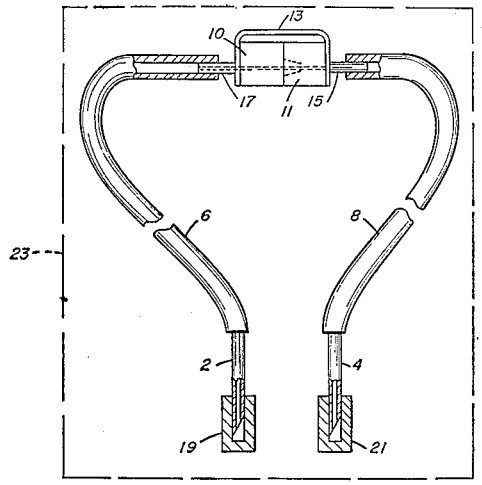

A dialyzing system incorporating needle cannulas for coupling a dialyzing apparatus to a patient by insertion of the needle cannulas into a patient's vein and associated artery, whereby the patient's blood is shunted through the system.

Figure 1:
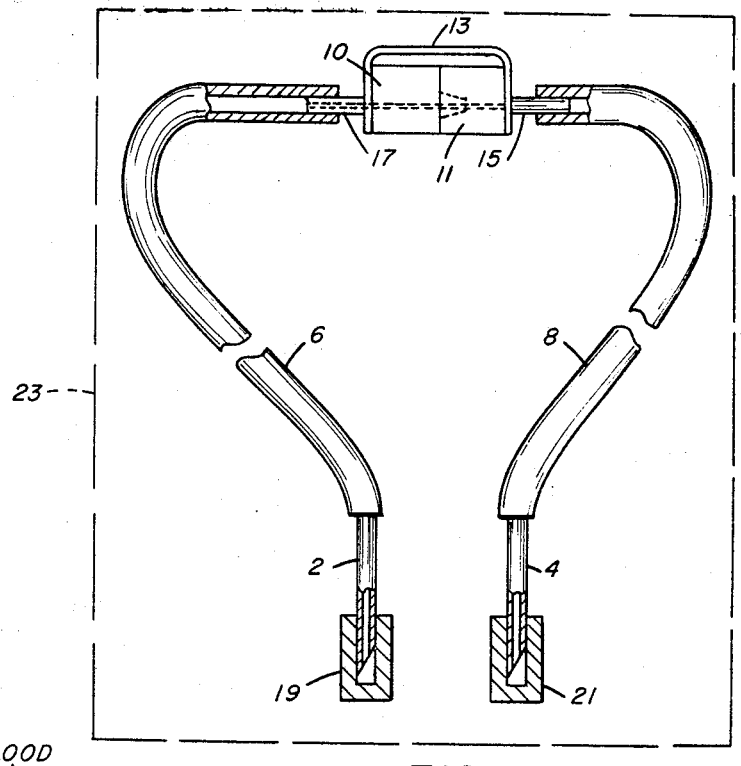

FIG. 1 shows a sterile container 3 enclosing a system wherein hollow needles 2 and 4 are carried in the ends of flexible tubes 6 and 8. The opposite ends of the tubes carry fittings 10 and 11 which are held together by a clip 13 so as to establish a shunt for blood flow when the system is removed from the container and the needles are inserted in a vein and artery of a patient.

Figure 2:
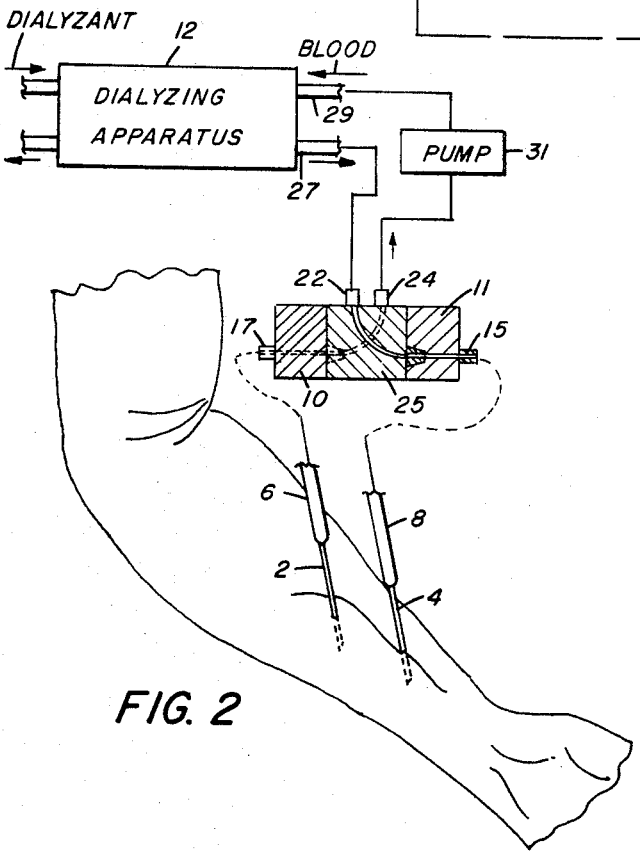

As shown in FIG. 2, after the shunt is established, the fittings 10 and 11 are disengaged and coupled to dialyzing apparatus 12, which acts as an artificial kidney.

Oct. 28, 1969 C. H. BENTON 762241 T867015 DEF. PUB.

MEANS AND METHOD OF HEMODIALYSIS

Filed Sept. 16, 1968

CHARLES H. BENTON
INVENTOR.

BY Wallace O. Fadeson
Paul D. Holmes
Henry M. Chapin
ATTORNEYS